US009243985B2

(12) United States Patent
Khonsari et al.

(10) Patent No.: US 9,243,985 B2
(45) Date of Patent: Jan. 26, 2016

(54) FRACTURE FATIGUE ENTROPY DETERMINATION

(75) Inventors: Michael M. Khonsari, Baton Rouge, LA (US); Mehdi Naderi Abadi, Baton Rouge, LA (US); Mehdi Amiri Darehbidi, Baton Rouge, LA (US)

(73) Assignee: Board of Supervisors of Louisiana State University And Agricultural and Mechanical College, Baton Rouge, LA (US)

( * ) Notice: Subject to any disclaimer, the term of this patent is extended or adjusted under 35 U.S.C. 154(b) by 1215 days.

(21) Appl. No.: 12/898,100

(22) Filed: Oct. 5, 2010

(65) Prior Publication Data

US 2012/0084019 A1  Apr. 5, 2012

Related U.S. Application Data

(60) Provisional application No. 61/248,522, filed on Oct. 5, 2009.

(51) Int. Cl.
*G01N 3/32* (2006.01)
*C22C 38/00* (2006.01)
*C22C 21/00* (2006.01)

(52) U.S. Cl.
CPC ........ *G01N 3/32* (2013.01); *C22C 38/00* (2013.01); *C22C 21/00* (2013.01); *G01N 2203/0005* (2013.01); *G01N 2203/0069* (2013.01); *G01N 2203/0073* (2013.01)

(58) Field of Classification Search
CPC ............ G01N 3/32; G01N 2203/0073; G01N 2203/0005; G01N 2203/0069
See application file for complete search history.

(56) References Cited

PUBLICATIONS

Mrozinksi, S., Metal Tests in Conditions of Controlled Strain Energy Density, Journal of Theoretical and Applied Mechanics, vol. 45, Ed. 4, p. 773-784 (2007).*
Luong, M., Fatigue Limit Evaluation of Metals Using an Infrared Thermographic Technique, Mechanics of Materials 28, pp. 155-163 (1998).*
Amiri, M. et al., "An Experimental Approach to Evaluate the Critical Damage," Int'l J. of Damage Mech, vol. 20, pp. 89-112 (2011).
Naderi, M. et al., "An experimental approach to low-cycle fatigue damage based on thermodynamic entropy," Int'l J. of Solids and Struc., vol. 47, pp. 875-880 (2010).
Naderi, M. et al., "A thermodynamic approach to fatigue damage accumulation under variable loading," Matl Sc and Eng, vol. A 527, pp. 6133-6139 (2010).
Naderi, M. et al., "Real-time fatigue life monitoring based on thermodynamic entropy," Struc. Health Monitoring OnlineFirst, pp. 1-9 (2010).

* cited by examiner

*Primary Examiner* — Manuel L Barbee

(57) ABSTRACT

A method and apparatus are disclosed for approximating in real time the fracture fatigue entropy (FFE) of a metallic object subjected to cyclic loading. Such objects experience fatigue, which can lead to failure after a number of loading cycles. The disclosed invention allows for real time monitoring of the entropy increase in a metallic object under cyclic loading, and allows for removing the object from service before fatigue fracture occurs. Through use of the present invention, users may keep metallic objects in service for longer periods, because such objects may be safely taken closer to the fatigue fracture point. The invention therefore can effectively extend the useful life of many critical components and reduce downtime resulting from repair or premature replacement.

1 Claim, 14 Drawing Sheets

FRACTURE FATIGUE ENTROPY DETERMINATION

CROSS-REFERENCE TO RELATED APPLICATION

The benefit of the Oct. 5, 2009 filing date of provisional patent application 61/248,522 is claimed under 35 U.S.C. §119 (e).

FIELD OF THE INVENTION

The invention relates to materials science and engineering, and in particular to the monitoring the service life of a metallic structure exposed to cyclic loading.

BACKGROUND OF THE INVENTION

All structures and machinery components undergoing fatigue loading are prone to crack formation and its subsequent growth that increases with time. When a crack is formed, the strength of the structure or the component is decreased and can no longer function in the intended manner for which it was designed for. Moreover, the residual strength of the structure decreases progressively with increasing crack size. Eventually, after a certain time the residual strength becomes so low that the structure fails. It is, therefore, of paramount importance to be able to predict accurately and in real time the rate of decline in the component's residual strength and the remaining life of the system.

Fracture mechanics is a branch of science that provides insights into the mechanism of failure and helps predict the service life of structures and machinery components. As depicted in FIG. 1, several disciplines are involved in the development of fracture mechanics. At the right end of the scale is the engineering load-stress analysis. Applied mechanics covers the analysis of crack tip stress fields as well as the elastic and plastic deformations of the material in the vicinity of the crack. Material science concerns itself with the fracture processes on the scale of atoms and dislocations in the form of impurities and grains.

In order to make a successful use of fracture mechanics in an engineering application, it is essential to have some knowledge of the total field shown in FIG. 1. Fatigue failure can occur only if—as a result of the presence of micro-cracks, local yielding, micro-cavities, etc.—the applied load produces an increase in the stress in a point (or a zone) of the material, with local values exceeding the elastic limit. It is known that if the stress is static, the local plasticization and the redistribution of the stress onto the surrounding material does not generate any particularly critical condition and the material reaches failure only under decidedly greater loads. On the contrary, in the case of cyclic loading, where the stress is one of fatigue, the material arrives at the condition of local yielding (micro-plasticization) and a micro-crack is generated. Hence, the repeated application of the stress leads to the crack propagation until, eventually, the condition of failure is reached and the specimen breaks.

The thermoelastic effect, which governs the relationship between the temperature variation and stress (or strain) change in the elastic range, has been well documented, and has been utilized to characterize the elastic stress field. Different means—such as thermocouples, thermistors, and thermography techniques—have been employed to monitor the temperature changes during mechanical tests. The thermoelastic stress analysis by thermography is now an advanced full-field stress measurement method. In materials undergoing cyclic loading, most of the dissipated energy due to hysteresis effects manifests itself as heat, and the heat is removed from the material by heat transfer.

Heat can be transferred by three processes: conduction, convection, and radiation. Conduction is the transfer of heat along a solid object. Convection transfers heat from the "wetted area" of a solid through the exchange of hot and cold molecules, e.g., air, water, etc. Radiation is the transfer of heat via electromagnetic (usually infrared, IR) radiation. Although these three processes can occur simultaneously, it is not unusual for one mechanism to overshadow the other two. If the fatigue experiment is rapid enough, which is generally true for low-cycle fatigue testing, the temperature rise can be surprisingly high. For fatigue tests at 1,000 Hz, for example, the temperature could increase 200° to 400° K above the initial temperature, depending on the material tested and specimen geometry.

Many researchers have attempted to quantify fatigue in order to predict the number of cycles to failure. Among them, Miner pioneered the idea of quantifying fatigue damage based on the hypothesis that under variable amplitude loading, the life fractions of the individual amplitudes sum to unity. Later, Coffin and Manson independently proposed the well-known empirical law $\Delta\epsilon_p/2 = \epsilon'_f(N_f)^c$ which relates the number of cycles to failure $N_f$ in the low-cycle fatigue regime to the amplitude of the applied cyclic plastic deformation, $\Delta\epsilon_p/2$, for a material with given mechanical properties, $\epsilon'_f$ and $c$. The role of energy dissipation associated with plastic deformation during fatigue loading as a criterion for fatigue damage was also investigated by Halford and Morrow.

The energy approach for estimating the fatigue life of materials under cyclic loading tests has gained considerable attention by researchers. Morrow's 1965 paper presents analysis that takes into account cyclic plastic energy dissipation and fatigue of metals that undergo cyclic loading. He presented a descriptive theory of fatigue that uses the cumulative plastic strain energy as a criterion for fatigue damage and the elastic strain energy as a criterion for fracture. For fully reversed fatigue load, Morrow derived a relation for plastic strain energy per cycle $W_p$ in terms of the cyclic stress-strain properties, applicable when plastic strain is predominant. Park & Nelson proposed an empirical correlation for estimation of fatigue life taking into account the elastic strain energy $W_e$ as well as plastic strain energy $W_p$. In the high-cycle regime, plastic strains are usually quite small and the $W_p$ approach becomes computationally unreliable. Park & Nelson further proposed that the two energy terms, $W_p$ and $W_e$, must be combined into the total strain energy parameter $W_t$, $$W_t = W_p + W_e = AN_f^\alpha + BN_f^\beta \tag{1}$$

where the constants A, α, B and β can be determined from a set of uniaxial fatigue test data that cover a sufficiently large number of cycles. The energy dissipation due to plastic deformation during fatigue is a fundamental irreversible thermodynamic process that must be accompanied by irreversible entropy gain.

Permanent degradations are the manifestation of irreversible processes that disorder a system and generate entropy in accordance to the second law of thermodynamics. Disorder in systems that undergo degradation continues to increase until a critical stage when failure occurs. Simultaneously with the rise in disorder, entropy monotonically increases. Thus, entropy and thermodynamic energies offer a natural measure of component degradation. It is desirable to quantify the entropy rise in bending, torsion, and tension-compression fatigue of metallic components, and particularly the entropy at the instance when fracture failure occurs. The present invention accomplishes this task. The entropy at the fracture point can be estimated by integrating the cyclic plastic energy per temperature of material. The present invention provides an accurate approximation of the total entropy at the instance of failure. This value is identified as the fracture fatigue entropy (FFE). Through use of the present invention, the FFE can be determined for a particular material. The FFE determined by the invention is a constant for a particular material, and is independent of frequency, load, and specimen size.

SUMMARY OF THE INVENTION

The present invention can be utilized in a number of embodiments. In a preferred embodiment, the invention includes a method for determining a fracture fatigue entropy (FFE) for a particular material. This method includes subjecting a specimen of the material to cyclical loading while monitoring the temperature of the specimen. The accumulated entropy is determined over time. The FFE is the total accumulated entropy at the point of a fracture failure of the specimen. This determination is preferably performed in a controlled lab setting, using an appropriate test platform.

Alternative embodiments include a method for monitoring the accumulated entropy over time and generating an appropriate signal when the accumulated entropy reaches a predetermined set point. This set point is set at some percentage of the FFE, and thus ensures the signal is generated prior to failure. The signal may be used to actuate a shut-off mechanism, thus automatically shutting down the machine when the accumulated entropy reaches the set point. Alternately, the signal may be sent to a warning, alarm, or other caution message to inform an operator that the machine or structure should be taken out of service.

Another embodiment of the invention includes a fatigue failure prevention unit (FPU). The FPU may include a computer programmed to calculate the accumulated entropy over time based on the temperature of the monitored component. A thermocouple or other temperature sensing device may be used to provide a temperature input, perhaps via a temperature data interface device, to the computer. One or more output signals may be generated to automatically shut-off the monitored item or to warn an operator that fatigue failure will occur unless the monitored item is shut down. It is possible, and may be preferable in some situations, to provide a warning signal at a lower threshold and then an automatic shut down signal if a higher threshold is reached.

DETAILED DESCRIPTION OF THE INVENTION

Fatigue tests were performed to evaluate the method of the present invention. Three different stress states examined are: completely reversed bending, completely reversed torsion and tension-compression loads. Tests were conducted with Aluminum 6061-T6 and Stainless Steel 304 specimens. The testing apparatus used is a compact, bench-mounted unit with a variable-speed motor, variable throw crank connected to the reciprocating platen, with a failure cut-off circuit in a control box, and a cycle counter. The variable throw crank is infinitely adjustable from 0 to 50.8 mm to provide different levels of stress amplitude. The same fatigue apparatus is used for applying torsion, bending and tension-compression loads using appropriate fixture.

Figure 1:
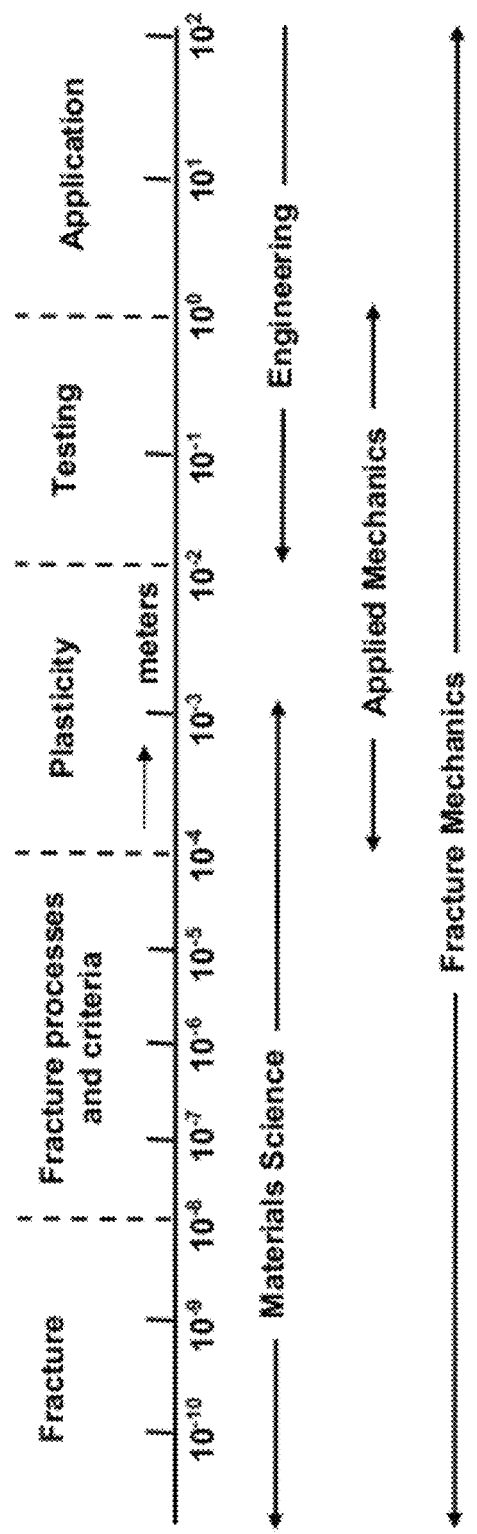
FIG. 1 is an illustration of the broad field of fracture mechanics.
Figure 2A:
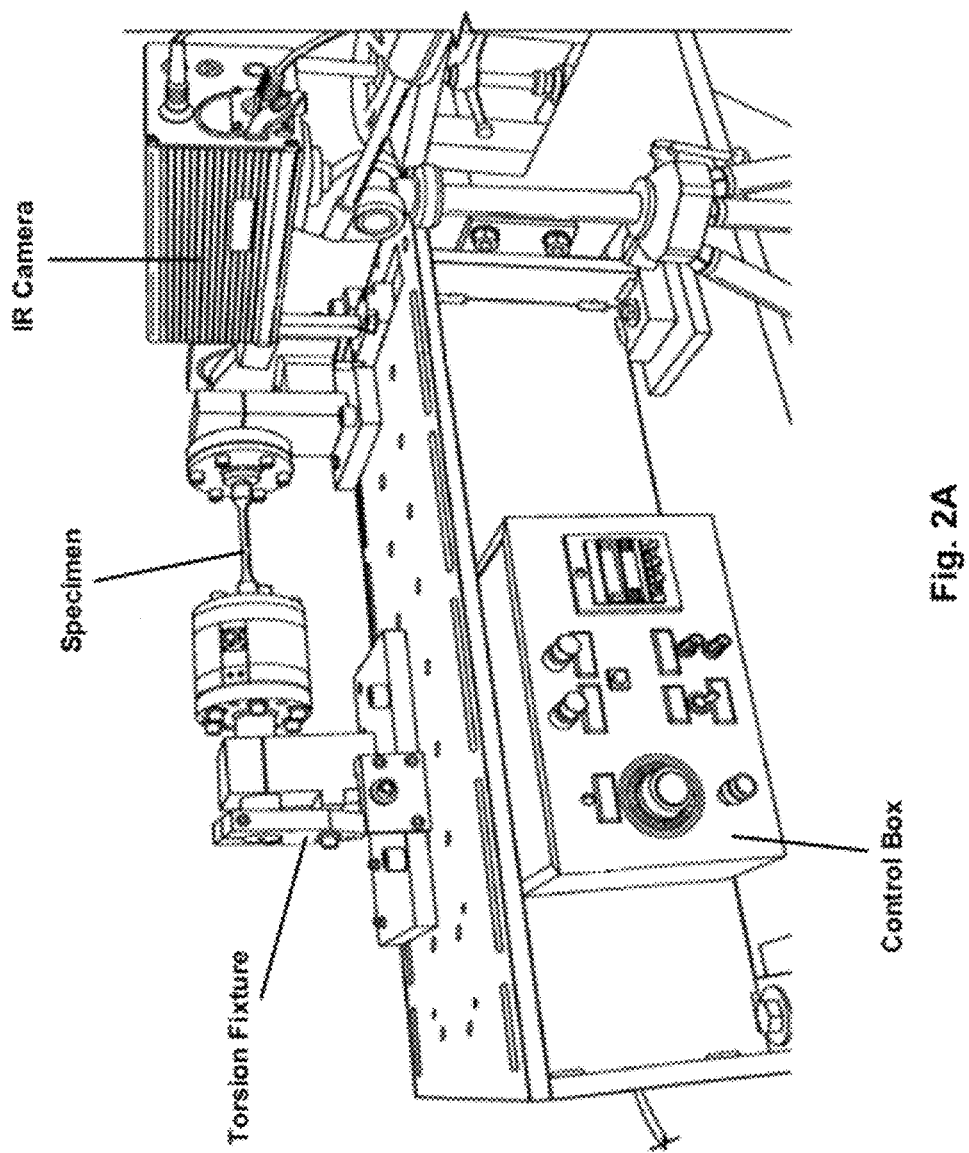
FIG. 2A is an illustration of experimental apparatus for torsion fatigue test.
Figure 2B:
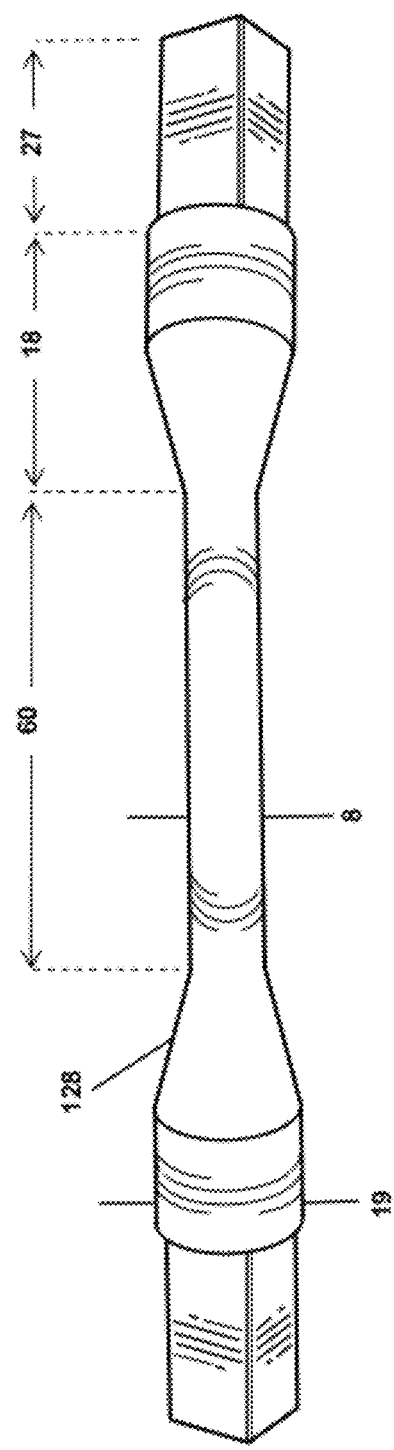
FIG. 2B is an illustration of a specimen used in torsion fatigue test.

FIG. 2 shows a schematic of the experimental setup used for torsion tests. The torsional fatigue tests are made using a round bar specimen clamped at both ends and rotationally oscillated at one of the ends via a crank with specified amplitude and frequency. Bending fatigue tests involve a plane specimen clamped at one end and oscillated at the other end, which is connected to the crank. The tension-compression fatigue tests involve clamping a plate specimen at both ends in the grips and oscillating the lower grip at a specified amplitude and frequency. All tests are conducted by installing a fresh specimen in the apparatus, specifying the operating condition, and running continuously until failure occurs. All tests are run until failure, when the specimen breaks into two pieces.

Figure 3:
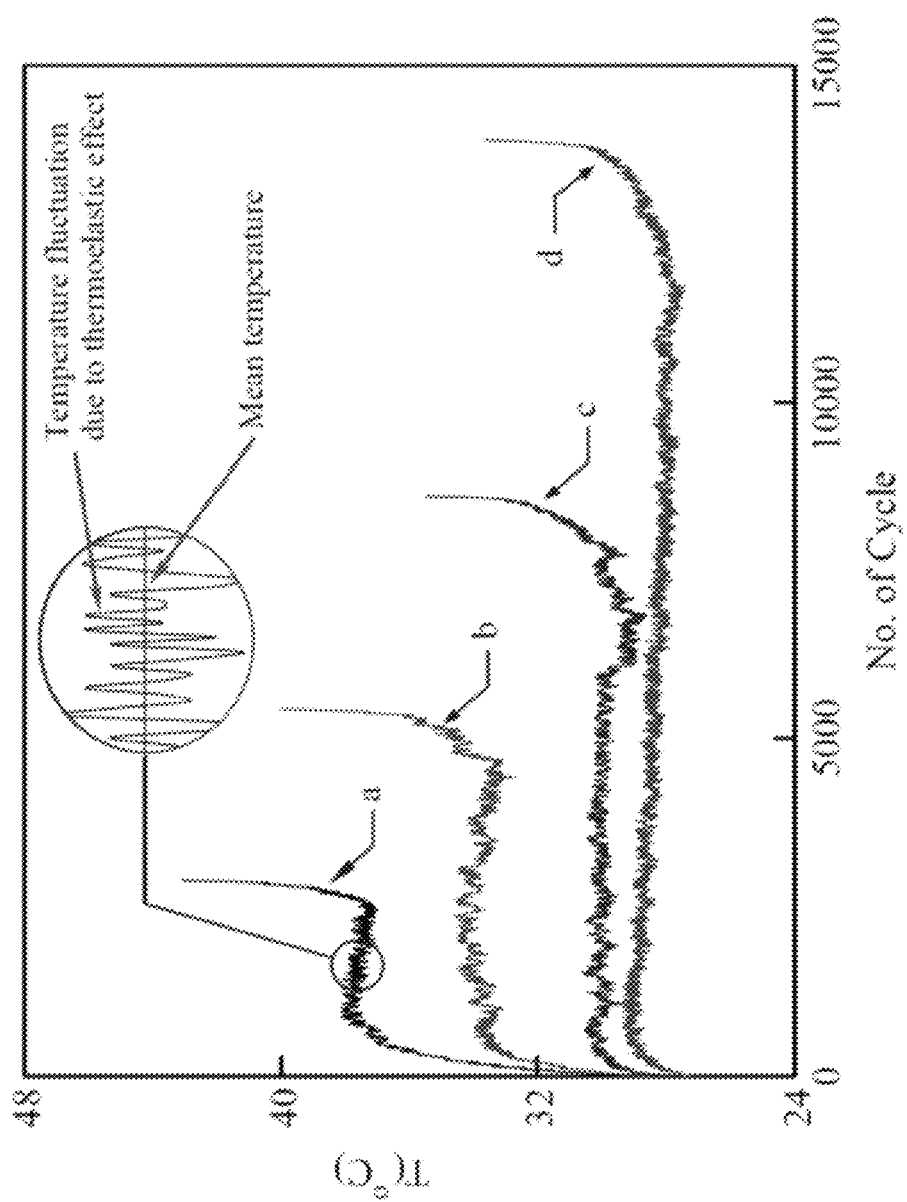
FIG. 3 is a temperature versus time plot for a series of fatigue tests.

High-speed, high-resolution infrared (IR) thermography was used to record the temperature evolution of the specimen during the entire experiment. Before fatigue testing, the surface of the specimen is covered with black paint to increase the thermal emissivity of the specimen surface. FIG. 3 shows surface temperature evolution of a series of bending fatigue tests at the clamped end where the specimen fractures. These tests pertain to subjecting an Aluminum specimen to different stress amplitudes.

Use of the present invention produces a consistent trend in all the fatigue tests. Initially, the surface temperature rises since the energy density associated with the hysteresis effect gives rise to generation of heat greater than the heat loss from the specimen by convection and radiation. Thereafter, temperature tends to become relatively uniform for a period of time until it suddenly begins to rise quite rapidly, just before failure occurs. FIG. 3 also shows how the temperature of the specimen varies around a mean value. The rise of the mean temperature during fatigue test is due to the plastic deformation of the material. The oscillation of the temperature around mean value is caused by the thermoelastic effect.

The processes at work in the specimens are irreversible and can be explained through use of the first and second laws of thermodynamic as applied to a system whose properties are a continuous function of space and time. According to the first law of thermodynamics the total energy content E within an arbitrary control volume can change only if energy flows into (or out of) the control volume through its boundary:

$$dE = dQ - dW \quad (2)$$

where Q and W are heat flow and work across the boundary of the control volume. In terms of the specific quantities, the law of conservation of energy for a control volume can be written as:

$$\rho \frac{du}{dt} = -\mathrm{div} J_q + \sigma D \quad (3)$$

where $\rho$ is density, u is specific internal energy, $J_q$ is heat flux across the boundary, $\sigma$ is symmetric stress tensor, and D is symmetric rate of deformation tensor.

The second law of thermodynamics (Clausius-Duhem inequality) postulates that the rate of entropy generation is always greater than or equal to the rate of heating divided by the temperature T. That is:

$$\rho ds/dt \geq -\mathrm{div}(J_q/T) \quad (4)$$

where s represents the specific entropy. The right hand side of equation 4 can be written as:

$$\mathrm{div}(J_q/T) = \mathrm{div}\, J_q/T - J_q \cdot \mathrm{grad}\, T/T^2 \quad (5)$$

Substituting equation 5 into equation 4 and replacing div $J_q$ from equation 3 yields:

$$\rho ds/dt + (\sigma D - \rho du/dt - J_q \cdot \mathrm{grad}\, T/T)/T \geq 0 \quad (6)$$

Let $\Psi$ represents the specific free energy defined as:

$$\Psi = u - Ts \quad (7)$$

Differentiating equation 7 with respect to time t, and dividing the result by temperature T yields:

$$-(d\Psi/dt + s\, dT/dt)/T = ds/dt - du/(T\, dt) \quad (8)$$

Considering equation (3.7), the inequality (3.5) reads:

$$(\sigma D - \rho(d\Psi/dt + s\, dT/dt) - J_q \cdot \mathrm{grad}\, T/T)/T \geq 0 \quad (9)$$

For small deformations, the deformation rate tensor D is replaced by $\dot{\epsilon}$ which represents the total strain rate. The total strain is decomposed to plastic and elastic strain:

$$\epsilon = \epsilon_p + \epsilon_e \quad (10)$$

The specification of the potential function (free specific energy $\Psi$) must be concave with respect to temperature T and convex with respect to other variables. Also, potential function $\Psi$ depends on observable state variables and internal variables:

$$\Psi = \Psi(\epsilon, T, \epsilon_p, \epsilon_e, V_k) \quad (11)$$

where $V_k$ can be any internal variable.

By referring to equation 10, strains are decomposed to $\epsilon - \epsilon_p = \epsilon_e$, so we can rewrite equation 11 as:

$$\Psi = \Psi(T, \epsilon - \epsilon_p, V_k) = \Psi(T, \epsilon_e, V_k) \quad (12)$$

Using the chain rule, the rate of specific free energy can be written as:

$$(13) \quad \partial\Psi/\partial t = (\partial\Psi/\partial\epsilon_e)\dot{\epsilon}_e + (\partial\Psi/\partial T)\dot{T} + (\partial\Psi/\partial V)\dot{V}$$

After substitution of equation 13 into equation 9, we obtain:

$$(\sigma\rho\partial\Psi/\partial\epsilon_e \dot{\epsilon} + \sigma\dot{\epsilon} - \rho(\partial\Psi/dT + s)\dot{T} - \rho\partial\Psi/\partial V_k \dot{V}_k - J_q \cdot \mathrm{grad}\, T/T)/T \geq 0 \quad (14)$$

For small strains, the following expressions define the thermoelastic laws:

$$\sigma = \rho\partial\Psi/\partial\epsilon_e \quad (15)$$

$$s = -\rho\partial\Psi/dT \quad (16)$$

The constructive laws of equations 15 and 16 arise from fulfillment of non-negative inequality of equations 14. By defining thermodynamic forces associated with the internal variables as follows:

$$A_k = \rho\partial\Psi/\partial V_k \quad (17)$$

Hence, the Clausius-Duhem inequality is reduced to express the fact that volumetric entropy generation rate is positive:

$$\dot{\gamma} = \sigma\dot{\epsilon}_p/T - A\dot{V}_k/T - J_q \cdot \mathrm{grad}\, T/T^2 \geq 0 \quad (18)$$

Equation 18 is also interpreted as the product of generalized thermodynamic forces $X = \{\sigma/T, A/T, \mathrm{grad}\, T/T^2\}$ and generalized rates or flows $J = \{\dot{\epsilon}_p, -\dot{V}_k, -J_q\}$:

$$\dot{\gamma} = \sum_k X_k \cdot J_k \quad (19)$$

Irreversible thermodynamics considers forces X as drivers of flows J. Each J can depend on all forces and intensive quantities (e.g., temperature T) associated with the dissipative process.

Equation 18 describes the entropy generation process which consists of the mechanical dissipation due to plastic deformation, nonrecoverable energy stored in the material, and the thermal dissipation due to heat conduction. For metals, the nonrecoverable energy represents only 5-10% of the entropy generation due to mechanical dissipation and is often negligible, thus allowing for further simplification of the computation:

$$A\dot{V}_k/T \approx 0 \quad (20)$$

Therefore, equation 18 reduces to:

$$\dot{\gamma} = \sigma\dot{\epsilon}_p/T - J_q \cdot \mathrm{grad}\, T/T^2 \geq 0 \quad (21)$$

The coupling of thermodynamics and continuum mechanics requires the selection of observable and internal variables. In the present study, two observable variables: temperature T and total strain $\epsilon$ are chosen. The first and second laws of thermodynamics, specific free energy as described in equations 3, 7, and 9, as well as Fourier's law ($J_q = -k\, \mathrm{grad}\, T$) lead to the following coupled thermomechanical equation:

$$k\nabla^2 T = \rho C\dot{T} - \sigma : \dot{\epsilon}_p - T\partial\sigma/\partial T \dot{\epsilon}_e \quad (22)$$

where k and $c_p$ are the thermal conductivity and specific heat, respectively.

Equation 22 shows the energy balance between four terms: transfer of heat by conduction ($k\nabla^2 T$); retardation effect due to thermal inertia ($\rho C\dot{T}$); internal heat generation consisting of plastic deformation ($W_p = \sigma : \dot{\epsilon}_p$)—which is responsible for mean temperature rise—; and, thermoelastic coupling term, $W_e = T\partial\sigma/\partial T \dot{\epsilon}_e$, which takes into account the thermoelastic effect (FIG. 3).

The total energy generation in equation 22 is the combination of elastic and plastic energy, $W_t = W_e + W_p$ for low and high-cycle fatigue.

$$W_t = 2(1+v)\sigma'^2_f N^{2b}/(3E) + 4\varepsilon'_f \left(\frac{1-n'}{1+n'}\right)\sigma_a^{(1+n')/n'}/\sigma'^{1/n'}_f \quad (23)$$

where n' is cyclic strain hardening exponent, $\varepsilon'_f$ is fatigue ductility coefficient, $\sigma'_f$ denotes the fatigue strength coefficient, $\sigma_a$ represents the stress amplitude and υ is the Poisson's ratio. The parameters b, E, and N represent the fatigue strength coefficient, modulus of elasticity and the number of cycles to failure, respectively.

Since the temperature fluctuation caused by thermoelastic effect is small in comparison with mean temperature rise (FIG. 3), the elastic part in equation 22 can be neglected. Therefore, equations 21 and 22 can be simplified to:

$$\rho C\dot{T} - k\nabla^2 T = W_p \quad (24)$$

$$\dot{\gamma} = W_p/T - J_q \cdot \text{grad } T/T^2 \geq 0 \quad (25)$$

The fracture fatigue entropy (FFE) can be obtained by integration of equation 25 up to the time $t_f$ when fracture occurs:

$$\gamma_f = \int_0^{t_f}(W_p/T - J_q \cdot \text{grad } T/T^2)dt \quad (26)$$

where $\gamma_f$ is FFE. In low-cycle fatigue where the entropy generation due to plastic deformation is dominant and the entropy generation due to heat conduction is negligible, equation 26 can be further reduced to:

$$\gamma_f = \int_0^{t_f}(W_p/T)dt \quad (27)$$

The cyclic plastic energy (the $W_p$ term in equation 27) is a function of several material properties including cyclic hardening exponent, fatigue ductility, and fatigue exponent. This term is relatively constant for a particular type of material and can be determined for each metal of interest. This value may then be used in equation 27, leaving on the temperature term to be determined.

The temperature of the metallic object of interest may be monitored using a thermocouple, IR imaging, or other suitable means. The temperature is then input to equation 27 on a real time basis, and the equation is solved, with the integral being evaluated from time zero until the time of fatigue failure. The FFE is determined in this manner, with the metallic object being subjected to the cyclic stress until failure.

Through use of the present invention, the FFE can be determined for any type of metal. As will be explained below, the FFE is relatively constant for a type of metal, and varies little with the type of load, frequency of loading, etc. This result is highly beneficial, because once the FFE is known for a particular material, the same process may be used on working equipment. When the calculated fatigue entropy of the working object (i.e., determined using equation 27) reaches a predetermined set point (e.g., 80% of FFE, or 90% of FFE), the machine or other item may be taken out of service, thus allowing use of a greater percentage of the object's total useful life without unduly increasing the risk of failure.

The invention, therefore, encompasses the method of determining either the FFE (on a test specimen) or the fatigue entropy (of a metallic object in use). The invention further encompasses use of the FFE to set a threshold for taking a working object out of service as the fatigue entropy approaches FFE. A particular system for performing this task is described below. But first, we turn to a description of a numerical simulation that can be used to support the approximations and assumptions relied upon in the invention.

Simultaneous solution of equations 24 and 26 is necessary to determine the entropy generation. For this purpose, a commercial software platform capable of solving partial differential equations may be utilized. FlexPDE was used to for the simulation conducted to confirm the accuracy and reliability of the present invention.

Three-dimensional models with ten-node quadratic tetrahedral elements and appropriate number of meshes for the specimens undergoing bending were developed for use in the numerical simulation. The corresponding number of finite elements for bending is 2709.

A mesh dependency study was carried out to investigate the effect of the number of meshes on the calculated entropy generation from equation 26. The results of the effect of mesh refinement for a bending test of an Aluminum-6061 specimen at 10 Hz and 49.53 mm displacement amplitude is shown in Table 1. The results show that the calculated FFE is relatively independent of mesh refinement.

Figure 5A:
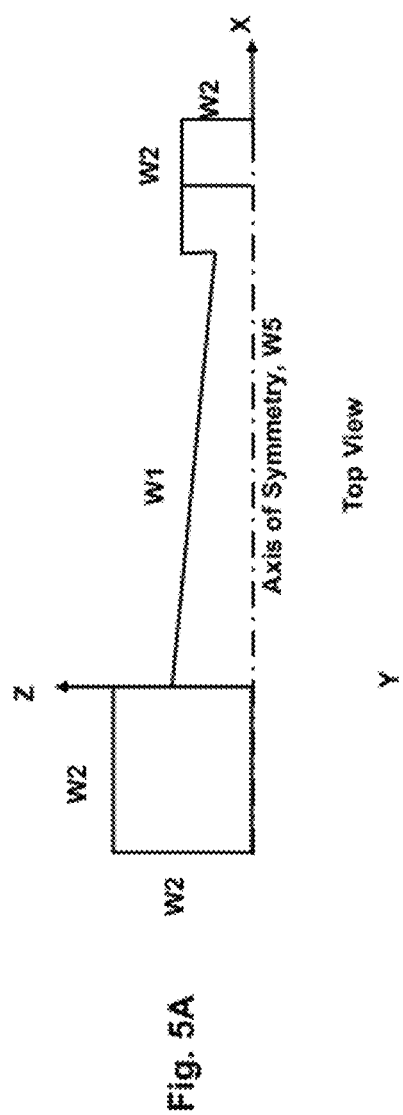
FIG. 5A is a top view of a boundary model used in the numerical simulation model.
Figure 5B:
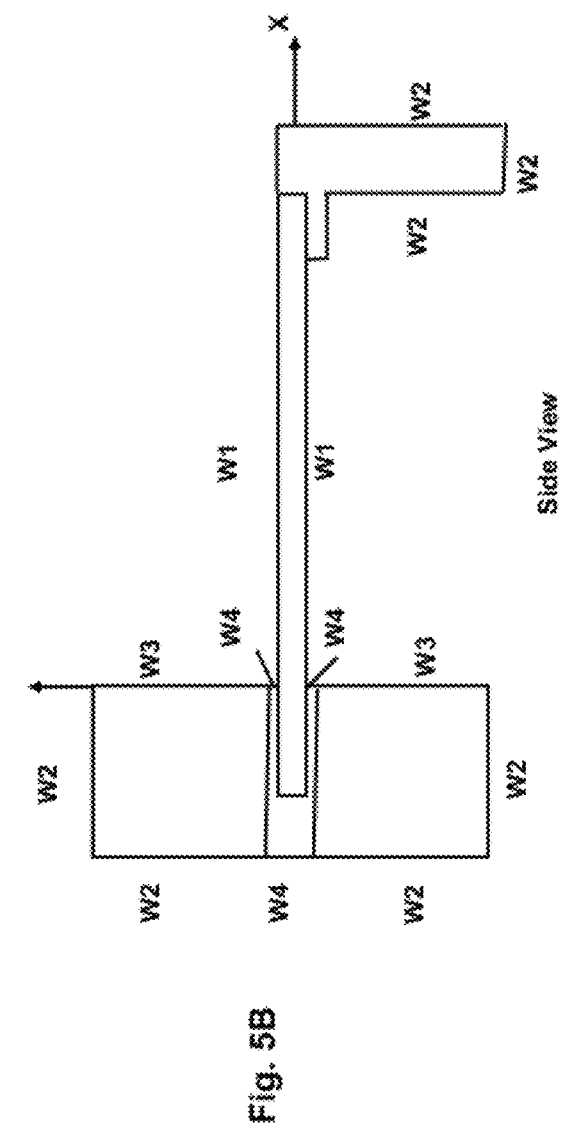
FIG. 5B is a side view of a boundary model used in the numerical simulation model.

FIGS. 5A and 5B show top and side views of a two dimensional sketch of the computational model used for the bending load with the notations indicating the boundary conditions. A summary of boundary conditions is shown in Table 2. Different tip displacement amplitudes (25-50 mm), and different loading frequencies (6-18 Hz) were considered as the applied loads in the model. Boundary W1 exchanges heat to the surroundings by convection and radiation. Walls W2 are at room temperature, $T_a$. Convective heat transfer is assumed as the boundary condition on walls W3. The convective heat transfer coefficient h is estimated using an experimental procedure which involves measuring the cooling rate of the specimen surface temperature after a sudden interruption of the fatigue test. Surface emissivity, $\epsilon_0$ is calculated to be 0.93 and $\sigma_0$ is the Stephan-Boltzman constant ($5.67 \times 10^{-8}$) (Wm$^{-2}$K$^{-4}$).

Walls W4 are associated with the glass wool insulation used in the experiments, thereby, zero heat flux is assumed at this boundary. The boundary W5 is considered as a symmetric boundary condition. Thermal and mechanical properties of the materials used in the experiments and models are summarized in Table 3.

TABLE 1

Effect of mesh refinement on calculated FFE

| No. of mesh | FFE (MJm$^{-3}$K$^{-1}$) |
|---|---|
| 2709 | 3.960 |
| 2897 | 3.955 |
| 5604 | 3.956 |
| 10771 | 3.954 |
| 15875 | 3.955 |

TABLE 2

Boundary conditions

| boundary | type | thermal condition | description |
|---|---|---|---|
| W1 | Wall, convection & radiation to air | $k\,\partial T/\partial n = h(T - T_a) + \sigma_0\epsilon_0(T^4 - T_a^4)$ | n is the normal to the wall |
| W2 | Wall, constant T | $T = T_a$ | |
| W3 | Wall, convection to air | $k\,\partial T/\partial n = h(T - T_a)$ | n is the normal to the wall |
| W4 | Wall, insulation | $\partial T/\partial n = 0$ | n is the normal to the wall |
| W5 | Wall, symmetric plane | $\partial T/\partial n = 0$ | n is the normal to the wall |

TABLE 3

| | | Material properties | | | | |
|---|---|---|---|---|---|---|
| material | k (Wm$^{-1}$K$^{-1}$) | ρ (kg m$^{-1}$) | C (Jkg$^{-1}$ K$^{-1}$) | σ' (Mpa) | ε' | n' |
| Al-6061 | 164 | 2659 | 871 | 535 | 1.34 | 0.095 |
| SS 304 | 16 | 7900 | 500 | 1000 | 0.25 | 0.171 |
| Glass wool | 0.037 | 200 | 0.66 | — | — | — |

Figure 6:
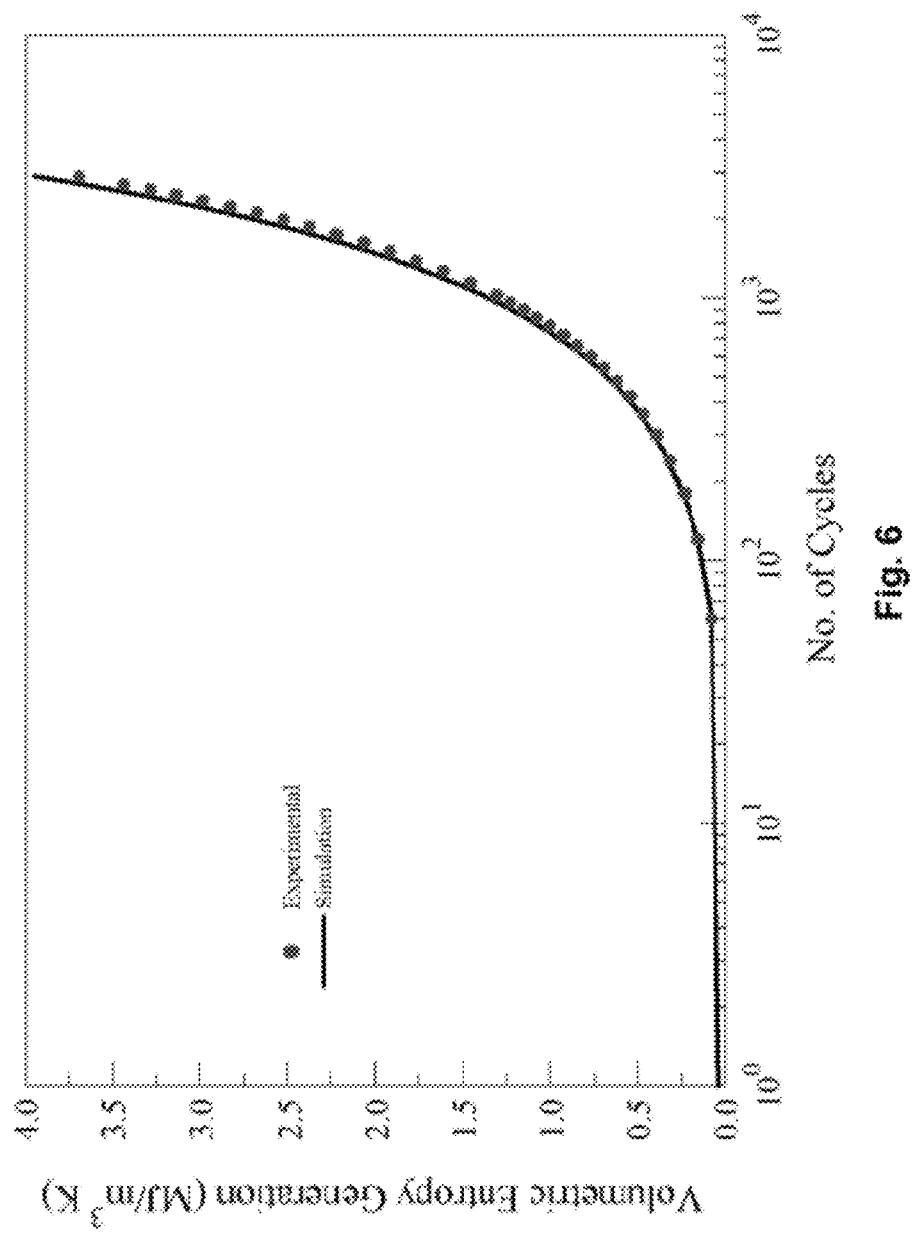
FIG. 6 is a plot showing the results of empirical tests and mathematic model using the method of the invention.

The evolution of entropy generation is calculated for the entire fatigue life and then integrated over time to determine the entropy generated during fatigue process (equation 26). FIG. 6 shows comparison of numerical and experimental entropy generation based on equations 26 and 27 for bending fatigue of Al 6061-T6-T6 where frequency and displacement amplitude are 10 Hz and 49.53 mm, respectively. The results predicted by the numerical simulation and those obtained empirically are quite consistent, confirming the accuracy of the present invention.

The small difference between the experimental results and numerical simulation is due to the fact that heat conduction is neglected in equation 27. The final value of the entropy generation (about 4 MJ/m$^3$K for this test) is associated with the entropy at fracture when the specimen breaks into two pieces. An uncertainty analysis was performed using the method of Kline and McClintock. The entropy calculation of the present invention results in an error of only about ±1%.

Figure 7:
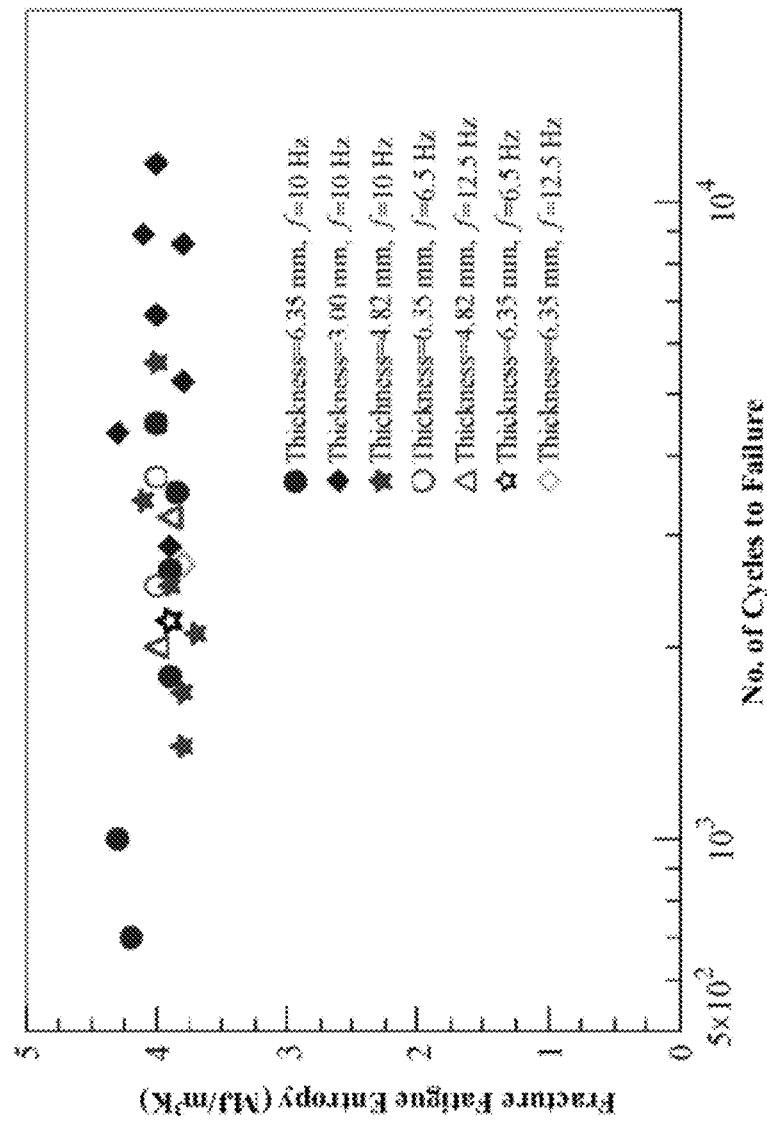
FIG. 7 is a plot showing the FFE for an Al 6061-T6 specimen under various conditions.

FIG. 7 shows the results of experimental FFE determinations for bending fatigue tests of an Al 6061-T6 test specimen at different frequencies. Results of different displacement amplitudes and different thicknesses of specimen, i.e., 3, 4.82, and 6.35 mm also are shown in this figure. The FFE, however, is consistent about 4 MJ/m$^3$K for this material, regardless of the load amplitude, load frequency, or specimen thickness. It is to be noted that the results of seven sets of experiments presented in FIG. 6 correspond to different combination of specimen thicknesses and operating frequencies. Also, experimental data are associated with the different displacement amplitudes ranging from 25 mm to 50 mm. The same concept for plotting experimental data is followed in FIGS. 8 and 9.

Figure 8:
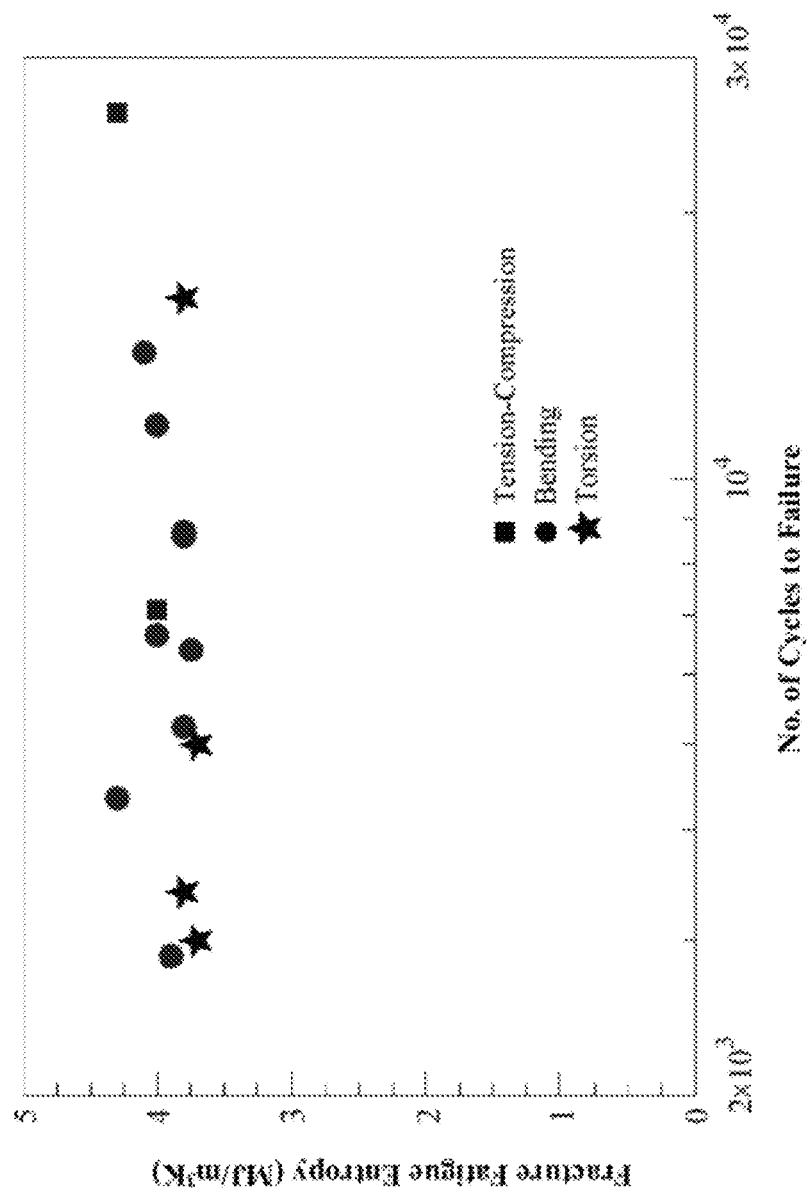
FIG. 8 is a plot showing the FFE for an Al 6061-T6 specimen under different types of loads.

FIG. 8 presents the FFE plotted as a function of the fatigue life for bending, torsion, and tension-compression fatigue tests for Al 6061-T6-T6 specimens at 10 Hz. It is seen that the FFE is independent of the type of loading, further confirming that use of the present invention allows determination of an FFE that is relatively constant for a particular type of material.

Figure 9:
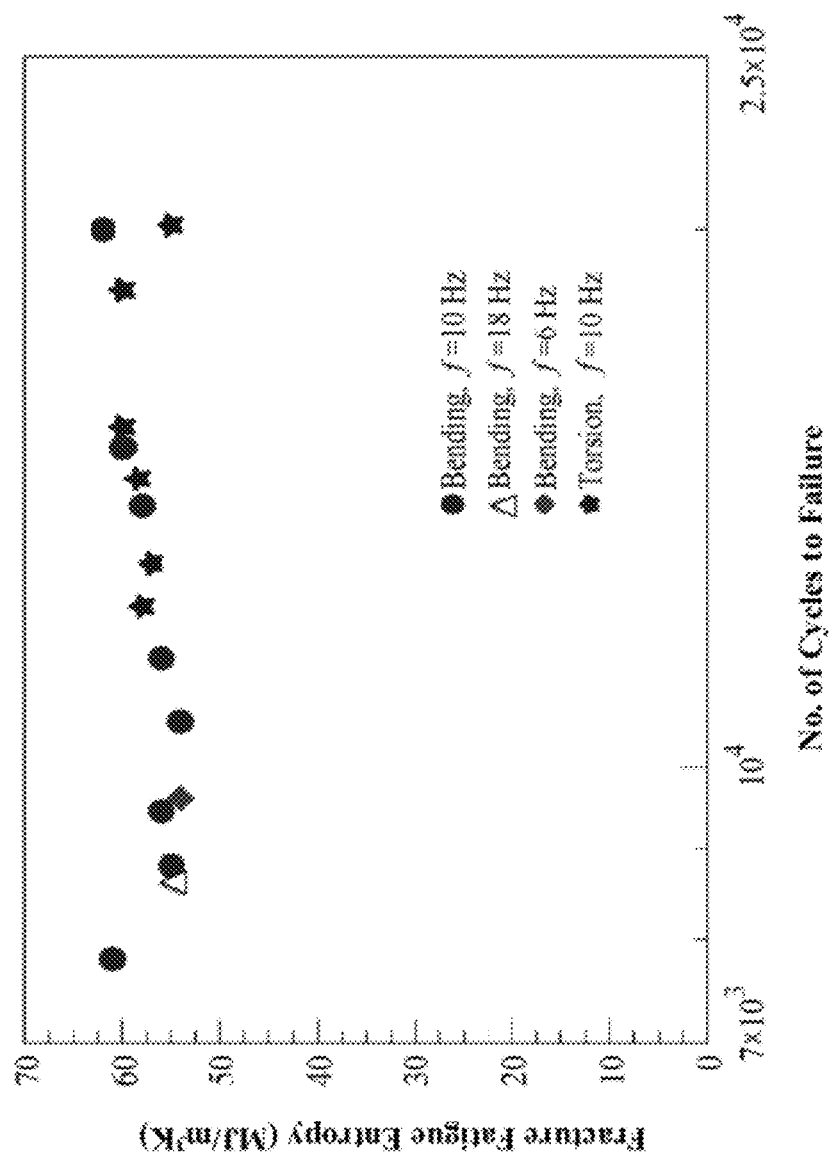
FIG. 9 is a plot showing the FFE for a SS 304 specimen under various conditions.

FIG. 9 presents the results of entropy generation at the fracture point for stainless steel 304 undergoing bending, and torsion fatigue tests. The results show that the entropy generation at the fracture point for SS 304 is about 60 MJ/m$^3$K, and is independent of frequency and geometry. It is to be noted that the fatigue life of a specimen undergoing cyclic load is only weakly dependent on the test frequencies up to 200 Hz.

The results presented in FIGS. 7-9 demonstrate the accuracy and value of the present invention. The FFE for the Aluminum and Stainless Steel specimens was constant. The results reveal that the necessary and sufficient condition for final fracture of Al 6061-T6-T6 corresponds to the entropy gain of 4 MJ/m$^3$K regardless of the test frequency, thickness of the specimen and the stress state. For SS 304 specimens, this condition corresponds to entropy gain of about 60 MJ/m$^3$K.

One embodiment of the present invention is a method and apparatus for prevention of catastrophic failure of metals undergoing fatigue load. As described above, (see FIG. 6), the entropy generation increases during the fatigue life toward a final value of $\gamma_f$ (i.e., the FFE). Thus, fracture fatigue entropy, FFE can be utilized as an index of failure. As the entropy generation accumulates toward the FFE, it provides the capability of shutting down of the machinery before a catastrophic break down occurs.

The typical prior art method used to avoid fatigue failure is based on rough estimates of the overall life expectancy of various components of a machine. A conservative threshold (e.g., 50% of full life) is then used to ensure that the machine is taken out of service before a fatigue failure occurs. This method is both wasteful and inaccurate. It typically results in equipment being taken out of service well before its full useful life has ended. This increases equipment cost and down time expenses.

This method also fails to make any real time determination of the remaining fatigue life of a piece of equipment. In some circumstances, a particular component may be subjected to substantially larger stresses than anticipated, thus reducing the component's fatigue lifespan. This type of situation may not be recognized when the prior art method is used, and a catastrophic fatigue failure may result.

The present invention provides a method of real time fatigue life determinations. Once the FFE has been determined using the present invention, the invention may be used to monitor, in real time, a piece of equipment in service. A threshold closer to the actual FFE (i.e., end of life) may safely be used with the present invention. Moreover, the fatigue life information produced by the present invention is real time and accurate. If a component is under excessive stress, the more rapid destruction of the component will be discovered if the present invention is used. A threshold of 90% of FFE may provide a sufficient safety margin in many applications.

The present invention relies upon the concept of constant entropy gain at the fracture point, $\gamma_f$, which is premised upon the assumption that thermodynamic conditions associated with the entropy generation are identical during the fatigue process and vary only with time. That is, failure occurs when $$N = N_f \gamma = \gamma_f \quad (28)$$

Within the range of the experimental tests performed, $\gamma_f$ was only dependent upon the material and is independent of load, frequency and thickness. Therefore, the duration of the fatigue process varies depending on the operating conditions in order to satisfy the condition of equation 28.

Based on this concept, one can conduct an accelerated failure testing scheme by increasing process rates J while maintaining equivalent thermodynamic forces X to obtain the same sequence of physical processes, in identical proportions, but at a higher rate. For example, by increasing frequency, the rate of plastic deformation $\dot{\epsilon}_p$ increases and subsequently the rate of degradation increases while the duration of the test is shortens in order to satisfy equation 28. This is in accordance with the accelerated testing procedure recently put forward by Bryant et al. based on the thermodynamics of degradation.

Figure 10:
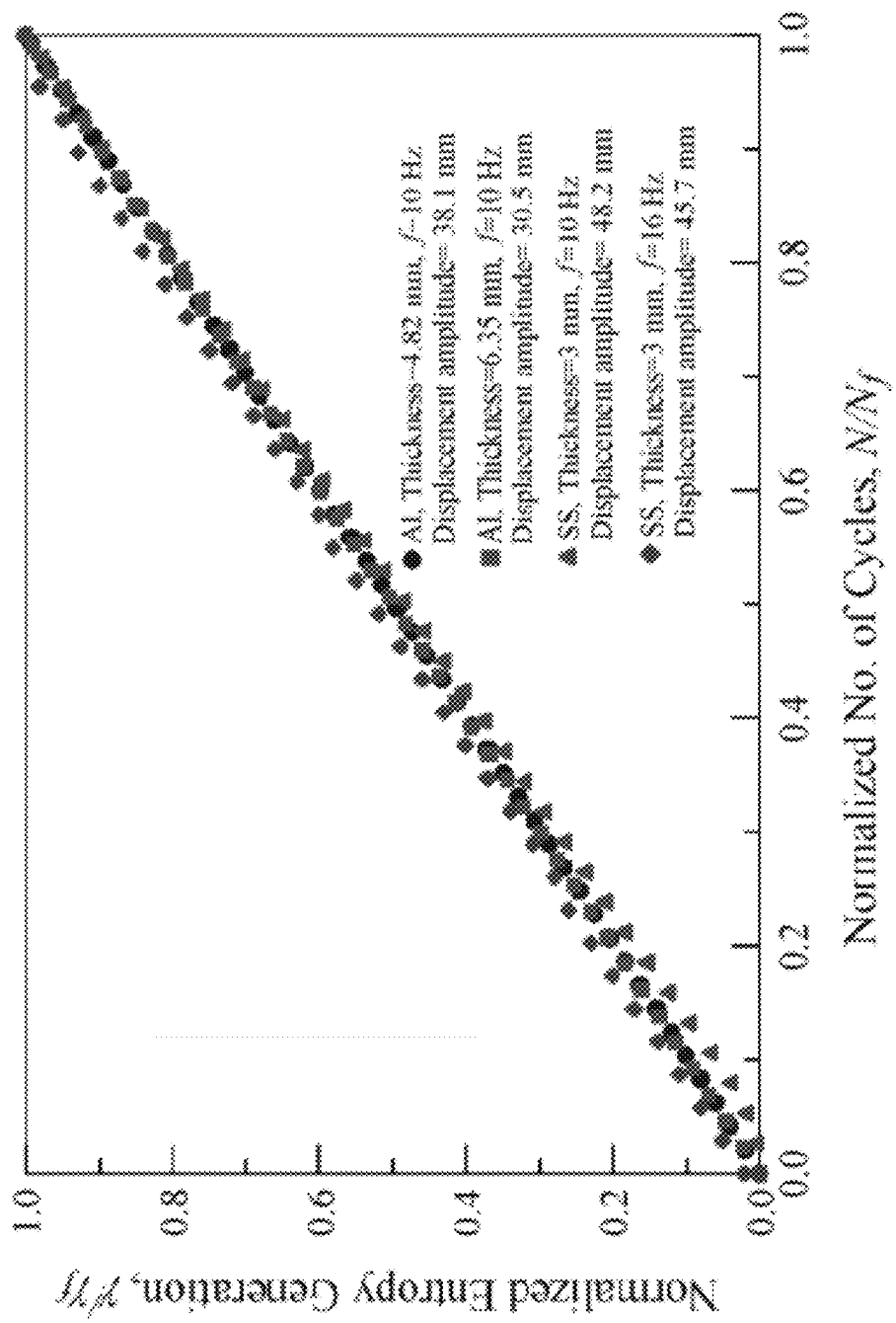
FIG. 10 is a plot of the normalized entropy generation versus normalized number of cycles for bending fatigue of Al 6061-T6 and SS 304 under various conditions.

FIG. 10 shows the normalized entropy generation during the bending fatigue of SS-304 and Al 6061-T6-T6 for different thicknesses, displacement amplitudes and frequencies. The abscissa of FIG. 10 shows the entropy generation using equation 26 and normalized by dividing by the entropy gain at the final fracture, $\gamma_f$. The ordinate shows the number of cycles normalized by dividing by the final number of cycles when failure occurs. It can be seen that normalized entropy generation monotonically increases until it reaches the entropy at the failure point. Interestingly, a similar trend between normalized wear plotted against the normalized entropy was reported by Doelling et al. Their work resulted in prediction of flow of the Archard's wear coefficient with remarkable accuracy.

The relation between the normalized cycles to failure and normalized entropy generation is approximately linear and can be described as follows:

$$\frac{\gamma}{\gamma_f} \cong \frac{N}{N_f} \quad (29)$$

where $\gamma_f$ is a property of material. Using equation 29, the number of cycles to failure can be expressed as:

$$N_f \cong \left(\frac{N}{\gamma}\right) \cdot \gamma_f \quad (30)$$

Equation 30 offers a methodology for prediction of the fatigue failure of a given material based on the measurement of the thermodynamic entropy generation. By having FFE, $\gamma_f$ and calculating entropy generation $\gamma$ at a selected number of cycles N, the fatigue life $N_f$ of the specimen can be predicted. Calculation of the entropy generation $\gamma$ can be performed at the very beginning number of cycles of the test, thereby providing an accelerated testing method for determination of fatigue failure.

A system may be constructed to monitor and protect equipment using the present invention. This system would be capable of continuously monitoring the health of a machine or a structure, providing signals to indicate remaining life, and triggering a signal to halt the operation when the remaining life falls below a specified desired value (e.g., 25%, 15%, or 10%). By halting operation when 75%, 85%, or 90% of the useful life has been expended, the system allows for longer use while avoiding catastrophic failure. To avoid failure, the following condition must be satisfied:

$$\frac{\gamma}{\gamma_f} \leq n \quad (31)$$

where n is the fraction of the total life chosen for the shut-off threshold. For example, if the shut-off is to occur at 90% of useful life, then n=0.90 in the above equation.

Figure 4:
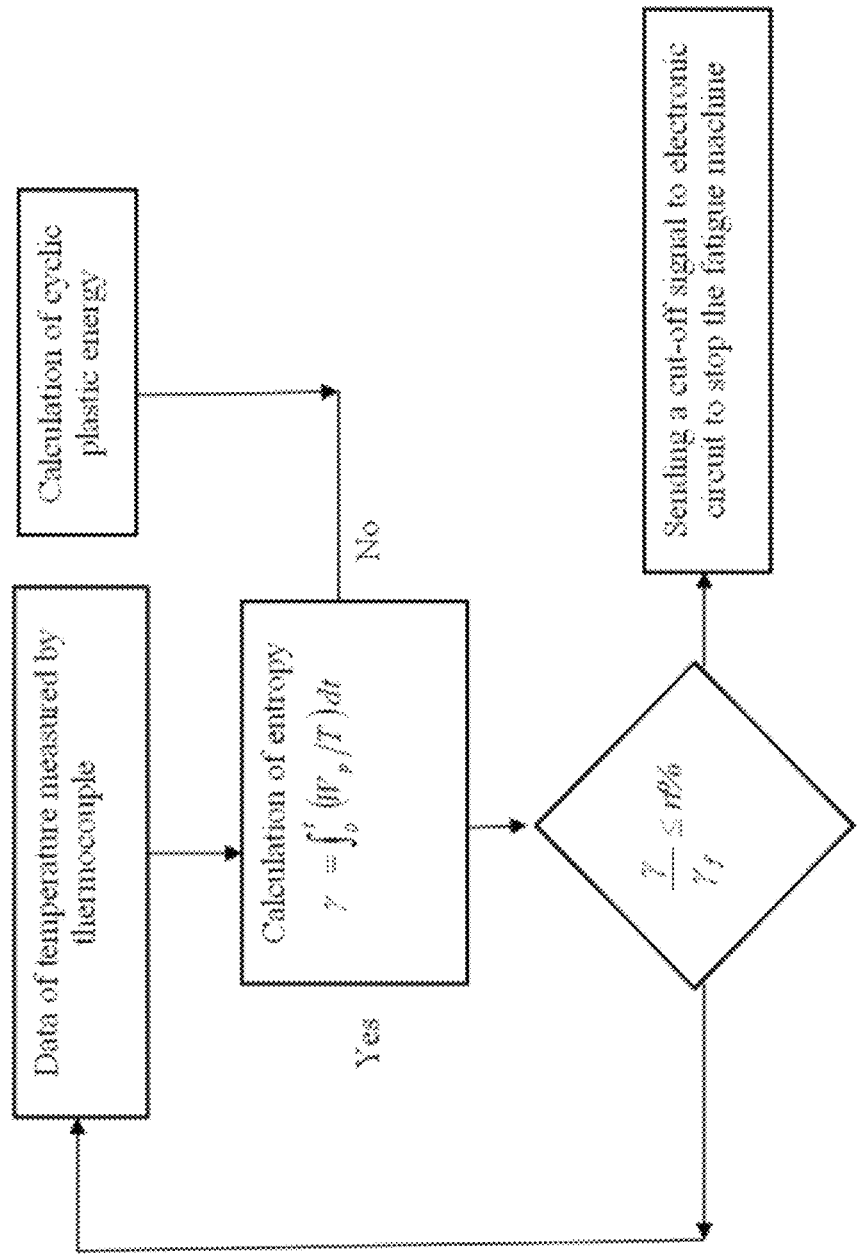
FIG. 4 depicts a flow chart representing a process in accordance with the present invention.

Using equation 27 above, the system may determine the accumulated entropy over time, where temperature of the specimen is the only external input required. As long as the ratio of the accumulated entropy over the FFE is less than the shut-off threshold, the system allows the equipment to remain in operation. Once that threshold is reached, the system either automatically shuts off the equipment or sends a warning signal to an operator who may then shut down the equipment. FIG. 4 depicts a flow chart representing the process.

This process may be implemented using software and other easily obtained items. A working embodiment of the invention was constructed using a fatigue test platform and a computer loaded with LabVIEW software. The process represented by the flow chart above is performed using the LabVIEW software. Other software platforms may be used, including by way of example, Eclipse and MatLab packages. Various other software platforms may also be available to perform these functions. The software choice is not critical to the invention.

A thermocouple was attached to the specimen to monitor temperature. Other means might also be used, including infrared monitoring or other temperature detection devices. The type of device used is not critical to the invention, so long as an accurate temperature signal is produced that is suitable for processing and input into the system. In the prototype system, an OMB-DAQ-56 was used to receive the temperature signal from the thermocouple and provide an appropriate temperature-based input signal to the computer for use by the programmed LabVIEW software.

A relay, switch, or other shut-off device may be used to automatically shut off the equipment when the accumulated entropy has reached the preset threshold level. In the prototype, an NI USB-9472 relay was used. This relay has a USB connection to interface with the computer. Other electronic circuits could be used as well to send a warning signal or to trigger an alarm for operators.

Figure 11:
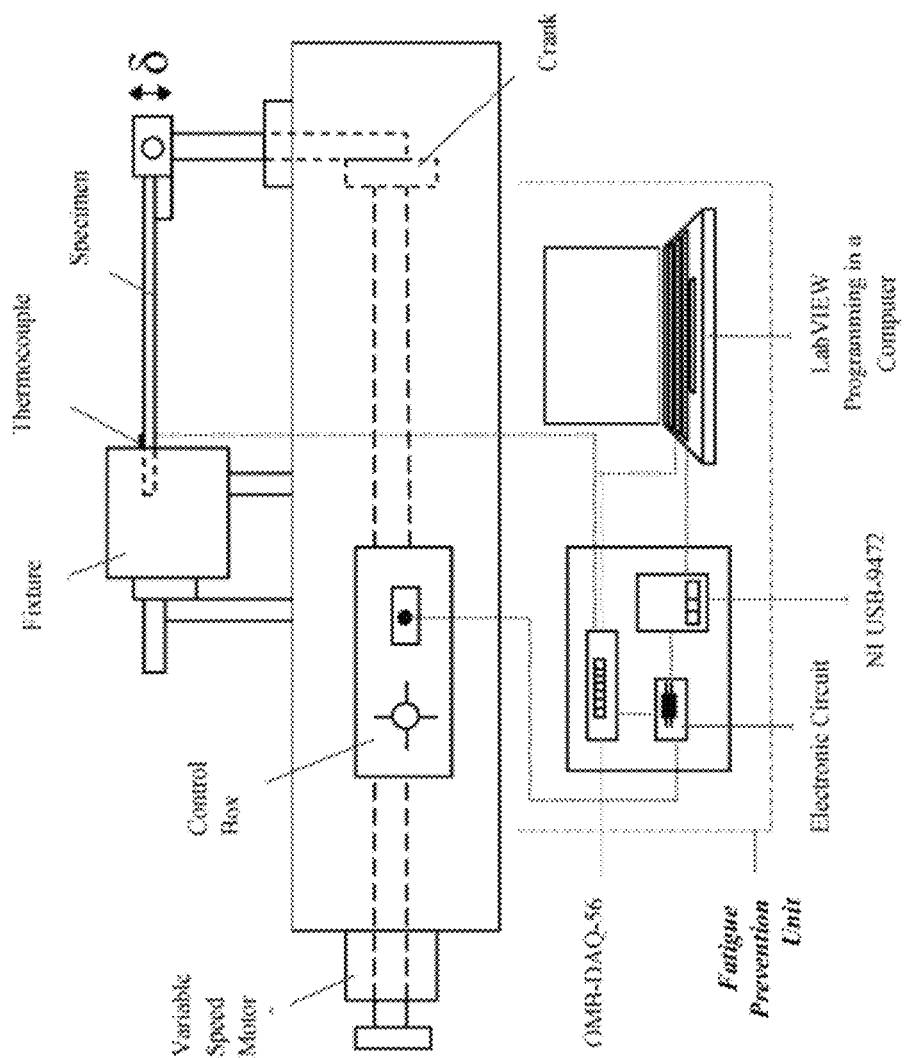
FIG. 11 is a schematic diagram of a prototype monitoring and shut-off system embodying the present invention.

FIG. 11 shows a schematic of the prototype. The fatigue test platform 10 is used to apply cyclic loading to a specimen 12. A thermocouple 14 is attached to the specimen and to an OMB-DAQ-56 temperature interface 16. The relay 18 is used to automatically shut off the fatigue test platform, but would shut off the monitored machine or structure in a real-world application. A computer 20 loaded with appropriately programmed software is also shown. An electronic circuit 22 is shown and could be used to send additional signals, such as alarm or warning signals for operators.

The system shown in FIG. 11 is a prototype. It is expected that the components of the system could be constructed in a single unit, a fatigue prevention unit (FPU) 24, which is shown within the dashed lines in FIG. 11. A preprogrammed microprocessor, temperature interface, and output interface could be constructed using off-the-shelf items or by designing and fabricating specialized chips for this purpose. An FPU that embodies the present invention could be a small device housed in a structure suitable for field use. A small, hardened and waterproof case could be used to house the FPU, so that the unit could be easily transported from one location to another.

It is further expected that the FPU could be designed as an integral component of certain equipment or structures. Consider, for example, a large pump used in an industrial setting. Such pumps can be extremely large and may include complex microprocessor-based controls. It would be a straightforward task for one skilled in the art to add the functional capabilities of the FPU to the existing controls of such a pump. Thermocouples or other suitable temperature monitoring devices could be factory installed on key components of the pump, with these devices providing real-time temperature data to the FPU. The pump, therefore, could be built at the factory with an integrated FPU and associated temperature-monitoring devices.

Another variation on the prototype system described above would be to provide a variable shut-off threshold control. In other words, the FPU would be constructed in a manner that allows an operator to set the shut-off threshold. This would allow individual users to select the shut-off threshold that makes the most sense for their situation. Where the consequences of failure are particularly severe, a more conservative threshold of perhaps 75% of useful life could be used. If the consequences of failure are less severe (e.g., in systems with redundant components), a higher threshold of perhaps 90% of useful life could be used. This capability would also allow operators to adjust the shut-off threshold based on their actual operating experiences.

The FPU may also be used to generate multiple signals in response to the accumulated entropy. A monitoring signal may be generated that provides information on a real-time basis of what percentage of useful life remains. A readout available to an operator may, for example, display the remaining life for each monitored piece of equipment. In addition, a warning light signal may be generated when a certain percentage of the useful life is met, an alarm signal when a higher percentage is met, and an automatic shut off signal when a still higher threshold is met.

To provide a more specific example of the multi-signal embodiment described above, consider a piece of equipment that is part of a larger operation. For example, a pump may be used to supply condensate to a boiler in an electrical power generation system. In this type of system, it may be important to secure the condensate pump as part of a larger, sequenced shut down operation. If the condensate pump were shut down without using the appropriate sequence, the boiler may quickly boil off all water, leaving its heating elements exposed and potentially causing damage. It such a setting, it would be highly desirable to avoid shutting down a condensate pump suddenly, and without performing the proper sequence of steps. In an extreme situation, such an unplanned shut down might cause the power plant to be out-of-service for an extended period. It also might result in a sudden and unexpected loss of electrical power, which could produce power outages to users.

The FPU could be configured to prevent these undesirable scenarios. A threshold of perhaps 75% of useful life could be used to generate a signal warning an operator that pump replacement will be required within hours, days, or perhaps even weeks. This warning would allow the operator and managers of the facility to plan for the replacement of the pump. Another, more urgent signal may be generated when the pump reaches 85% of its useful life, perhaps triggering a visual caution light and an audible alarm. If the pump remained in service, and reached 90% of useful life, an automatic shut off signal might be appropriate if the potential damage caused by a pump failure is greater than that caused by an unplanned shut down of a pump. These types of decisions will depend on the particular circumstances of each use. The important point is that the present invention, as embodied in an FPU, would allow for a protection system tailored to each situation's unique needs.

The FPU concept may be of particular interest to organizations responsible for maintaining large structures such as bridges. By monitoring accumulated fatigue entropy, it would be possible to secure such structures before fatigue failures occur. The automated monitoring capabilities and the accuracy of an FPU embodying the present invention would reduce the need for on-site inspections and would provide a more accurate and reliable measure of the soundness of the structure. A physical inspection may miss very small cracks, particularly if they are obstructed by other items. The FPU, on the other hand, would be able to monitor entire components and would not be limited by the ability of an inspector to see physical signs of impending fatigue failure.

Natural resource exploration may also be a particularly good application for the present invention. Oil and gas exploration wells are being drilled to great depths, including several miles below the seafloor. In these operations, it takes a great deal of time to remove the entire drill string from the bore hole. Each section of drill pipe must be disconnected and stored as the drill string is removed from the bore hole. When several miles of drill string are used, this operation becomes quite time consuming and expensive.

A failure of the drilling or exploration equipment within the bore hole, however, can be catastrophic, because the entire drill string may be lost in the hole. This may result in a complete loss of the entire operation, requiring the operator to start over. The cost of such a failure is enormous, and for that reason, operators must remove and replace downhole equipment well before it reaches the point of fatigue failure.

The present invention might allow operators to safely utilize more of the useful life of the downhole equipment. That would reduce the need to pull the entire drill string out of the borehole, thus saving a great deal of time and money. It would also reduce the risk of downhole failure by providing actual fatigue information, rather than requiring reliance on estimated life. The value of these benefits could be quite substantial. In this industrial context, it might be well worth building FPUs into the downhole equipment, so that the needed temperature data is transmitted to operators in real time. Data is currently provided during the drilling operation using logging-while-drilling (LWD) equipment. Including temperature data on the drillstring components would allow use of integral FPUs in this context.

The prototype FPU was used to confirm the operation of the present invention. Temperature evolution of two different constant load amplitudes during fatigue is plotted in FIG. 12. Entropy accumulation is calculated in the fatigue prevention unit and compared with FFE. As long as accumulated entropy is below the defined fatigue life (90% of life), the specimen under fatigue is on the safe side. To illustrate, we set the threshold to 90% of life, and allowed the PFU to automatically shuts down the fatigue apparatus, stage 1 in FIG. 12. Then, to further illustrate the utility of PFU, the fatigue test is continued again and verified that after another 10%, fracture occurs, stage 2 in the FIG. 12.

Figure 12:
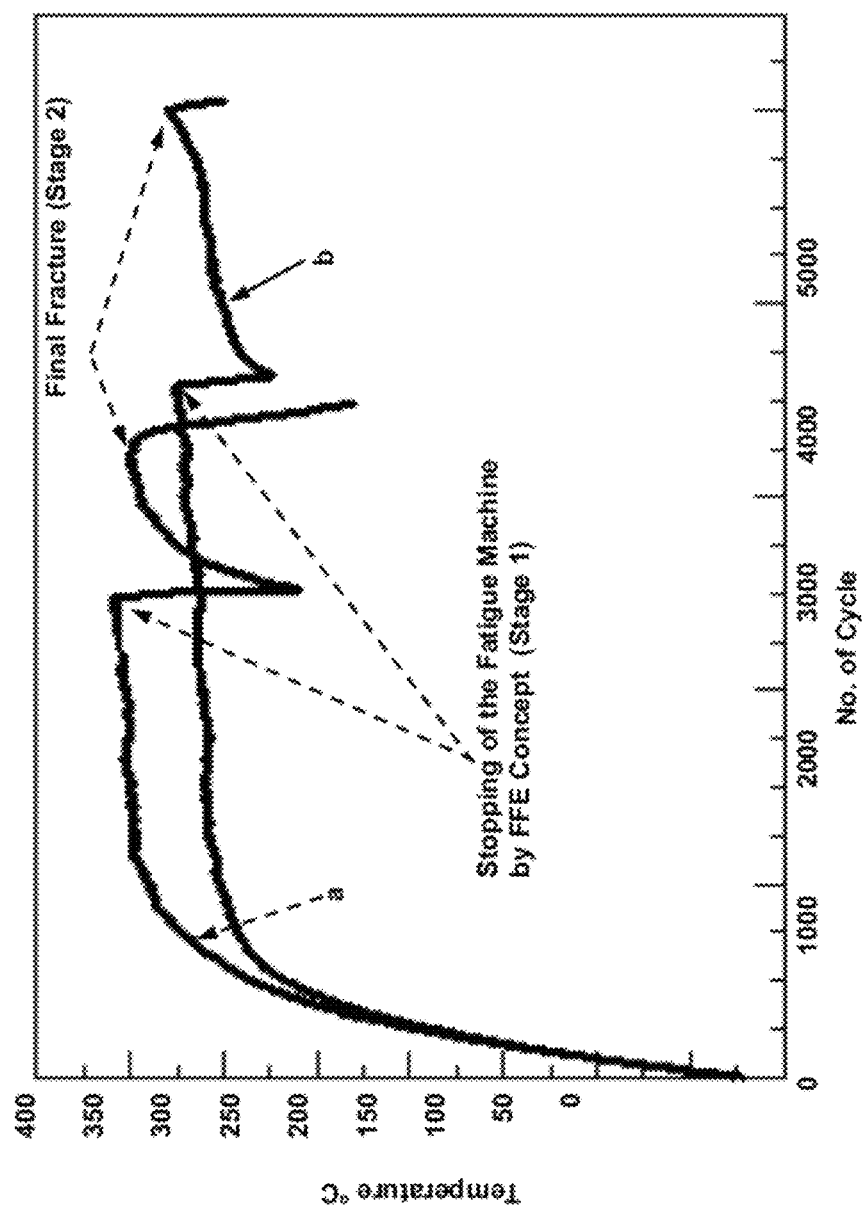
FIG. 12 is a plot of temperature vs. fatigue life for an FPU prototype testing SS 304.

FIG. 12 depicts temperature evolution vs. fatigue life for torsion test of SS 304 under constant load. a) 35.56 mm displacement amplitude load, b) 33.02 mm displacement amplitude load. As soon as accumulated entropy reaches to 90% of life, fatigue prevention unit shuts down the fatigue machine.

Figure 13:
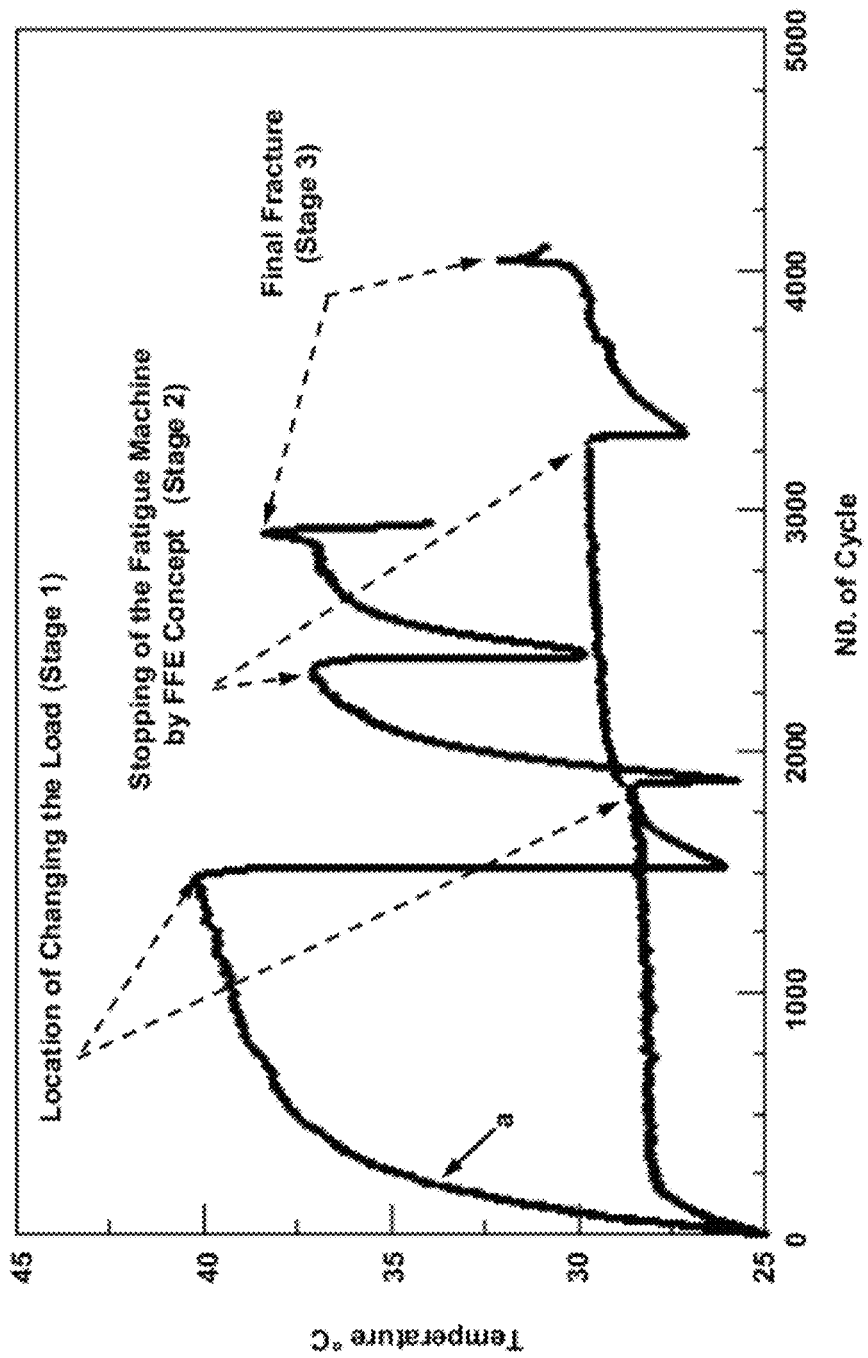
FIG. 13 is a plot of a temperature vs. fatigue life for an FPU prototype testing Al 6061-T6.

FIG. 13 depicts temperature variation of Aluminum specimen under two different variable load amplitudes. Entropy is accumulated up to stage 1 which is the location of changing the load. Then the accumulated entropy is added to the accumulation entropy at stage 2 where fatigue test is stopped. The continuation of the experiment up to stage 3 proves that the remaining life is close to the 10%. The capability of the present invention to accurately predict failure even under variable load conditions is a significant benefit of the invention.

FIG. 13 depicts Temperature evolution vs. fatigue life for bending test of Al 6061-T6-T6 under variable load. a) High to low load amplitude (44.45 to 36.83 mm), b) Low to high load amplitude (36.83 to 44.45 mm). As soon as accumulated entropy reaches to 90% of life, fatigue prevention unit shuts down the fatigue machine.

While the preceding description is intended to provide an understanding of the present invention, it is to be understood that the present invention is not limited to the disclosed embodiments. To the contrary, the present invention is intended to cover modifications and variations on the structure and methods described above and all other equivalent arrangements that are within the scope and spirit of the following claims.

We claim:

1. A method for preventing the mechanical failure of a metallic object; wherein the metallic object is subject to cyclic loading; and wherein said method comprises the following steps:
   (a) measuring the temperature of the surface of the metallic object, in the vicinity of the location of incipient mechanical failure, using a temperature sensor;
   (b) approximating the accumulated volumetric entropy production $\gamma$ in the vicinity of the location of incipient mechanical failure of the metallic object, using a relationship that is equivalent to:

$$\gamma = \int_0^{t'} (W_p/T) dt$$

wherein t denotes the time, t' denotes the particular time for which $\gamma$ is being determined, T denotes the temperature of the surface of the metallic object in the vicinity of the location of incipient mechanical failure, and Wp denotes the cyclic plastic energy for the metallic object;
   (c) predicting the time of mechanical failure of the metallic object when $\gamma$ is approaching the value of $\gamma_f$, or is approaching a user-specified fraction of the value of $\gamma_f$, wherein $\gamma_f$ denotes the mean volumetric fracture fatigue entropy for the metallic object; and
   (d) stopping the cyclic loading of the metallic object, using a controller, when $\gamma$ approaches the value of $\gamma_f$, or when $\gamma$ approaches a user-specified fraction of the value of $\gamma_f$.

* * * * *